(12) United States Patent
Rabinowitz et al.

(10) Patent No.: US 7,988,952 B2
(45) Date of Patent: *Aug. 2, 2011

(54) DELIVERY OF DRUG ESTERS THROUGH AN INHALATION ROUTE

(75) Inventors: Joshua D. Rabinowitz, Princeton, NJ (US); Alejandro C. Zaffaroni, Atherton, CA (US)

(73) Assignee: Alexza Pharmaceuticals, Inc., Mountain View, CA (US)

( * ) Notice: Subject to any disclaimer, the term of this patent is extended or adjusted under 35 U.S.C. 154(b) by 592 days.

This patent is subject to a terminal disclaimer.

(21) Appl. No.: 12/057,330

(22) Filed: Mar. 27, 2008

(65) Prior Publication Data

US 2008/0175796 A1    Jul. 24, 2008

Related U.S. Application Data

(63) Continuation of application No. 11/488,943, filed on Jul. 18, 2006, now abandoned, which is a continuation of application No. 10/749,783, filed on Dec. 30, 2003, now Pat. No. 7,078,019, which is a continuation of application No. 10/146,516, filed on May 13, 2002, now Pat. No. 6,737,042.

(60) Provisional application No. 60/294,203, filed on May 24, 2001, provisional application No. 60/317,479, filed on Sep. 5, 2001.

(51) Int. Cl.
*A61K 9/12* (2006.01)
*A61K 9/14* (2006.01)
*A61M 15/00* (2006.01)

(52) U.S. Cl. ............ 424/45; 424/46; 424/489; 424/434; 424/499; 514/958; 128/200.14; 128/200.24; 128/203.15

(58) Field of Classification Search .................. 424/45, 424/46, 489, 434, 499; 514/958; 128/200.14, 128/200.24, 203.15
See application file for complete search history.

(56) References Cited

U.S. PATENT DOCUMENTS

| | | |
|---|---|---|
| 3,164,600 A | 1/1965 | Janssen et al. |
| 3,219,533 A | 11/1965 | Mullins |
| 3,560,607 A | 2/1971 | Hartley et al. |
| 3,894,040 A | 7/1975 | Buzby, Jr. |
| 3,949,743 A | 4/1976 | Shanbrom |
| 3,982,095 A | 9/1976 | Robinson |
| 3,987,052 A | 10/1976 | Hester, Jr. |
| 4,141,369 A | 2/1979 | Burruss |
| RE30,285 E | 5/1980 | Babington |
| 4,229,447 A | 10/1980 | Porter |
| 4,303,083 A | 12/1981 | Burruss, Jr. |
| 4,376,767 A | 3/1983 | Sloan |
| 4,423,071 A | 12/1983 | Chignac et al. |
| 4,474,191 A | 10/1984 | Steiner |
| 4,484,576 A | 11/1984 | Albarda |
| 4,508,726 A | 4/1985 | Coleman |
| 4,566,451 A | 1/1986 | Badewien |
| 4,588,721 A | 5/1986 | Mahan |
| 4,654,370 A | 3/1987 | Marriott, III et al. |
| 4,708,151 A | 11/1987 | Shelar |
| 4,734,560 A | 3/1988 | Bowen |
| 4,735,217 A | 4/1988 | Gerth et al. |
| 4,819,665 A | 4/1989 | Roberts et al. |
| 4,848,374 A | 7/1989 | Chard et al. |
| 4,853,517 A | 8/1989 | Bowen et al. |
| 4,863,720 A | 9/1989 | Burghart et al. |
| 4,895,719 A | 1/1990 | Radhakrishnun et al. |
| 4,906,417 A | 3/1990 | Gentry |
| 4,917,119 A | 4/1990 | Potter et al. |
| 4,917,120 A | 4/1990 | Hill |
| 4,924,883 A | 5/1990 | Perfetti et al. |
| 4,941,483 A | 7/1990 | Ridings et al. |
| 4,963,289 A | 10/1990 | Ortiz et al. |
| 5,017,575 A | 5/1991 | Golwyn |
| 5,042,509 A | 8/1991 | Banerjee et al. |
| 5,049,389 A | 9/1991 | Radhakrishnun |
| 5,060,671 A | 10/1991 | Counts et al. |
| 5,099,861 A | 3/1992 | Clearman et al. |
| 5,112,598 A | 5/1992 | Biesalski |
| 5,126,123 A | 6/1992 | Johnson |
| 5,135,009 A | 8/1992 | Muller et al. |
| 5,144,962 A | 9/1992 | Counts et al. |
| 5,146,915 A | 9/1992 | Montgomery |

(Continued)

FOREIGN PATENT DOCUMENTS

EP    0 039 369    11/1981

(Continued)

OTHER PUBLICATIONS

U.S. Appl. No. 11/687,466, filed Mar. 16, 2007, Zaffaroni et al.
U.S. Appl. No. 11/964,630, filed Dec. 26, 2007, Hale et al.
U.S. Appl. No. 12/045,674, filed Mar. 10, 2008, Wensley.
U.S. Appl. No. 12/111,188, filed Apr. 28, 2008, Hale et al.
U.S. Appl. No. 12/117,737, filed May 8, 2008, Hale et al.
Office Action mailed Dec. 4, 2003 with respect to U.S. Appl. No. 10/057,198.
Office Action mailed Sep. 20, 2005 with respect to U.S. Appl. No. 10/057,198.
Office Action mailed Jul. 3, 2006 with respect to U.S. Appl. No. 10/057,198.
Office Action mailed Jan. 26, 2007 with respect to U.S. Appl. No. 10/057,198.
Office Action mailed Dec. 15, 2003 with respect to U.S. Appl. No. 10/057,197.
Office Action mailed Jun. 3, 2004 with respect to U.S. Appl. No. 10/057,197.

(Continued)

*Primary Examiner* — Mina Haghighatian
(74) *Attorney, Agent, or Firm* — Swanson & Bratschun, L.L.C.

(57) ABSTRACT

The present invention relates to the delivery of drug esters through an inhalation route. Specifically, it relates to aerosols containing drug esters that are used in inhalation therapy. In a method aspect of the present invention, a drug ester is delivered to a patient through an inhalation route. The method comprises: a) heating a composition, wherein the composition comprises a drug ester, to form a vapor; and, b) allowing the vapor to cool, thereby forming a condensation aerosol comprising particles with less than 5% drug ester degradation product. In a kit aspect of the present invention, a kit for delivering a drug ester through an inhalation route is provided which comprises: a) a thin coating of a drug ester composition and b) a device for dispensing said thin coating as a condensation aerosol.

24 Claims, 1 Drawing Sheet

U.S. PATENT DOCUMENTS

| | | |
|---|---|---|
| 5,166,202 A | 11/1992 | Schweizer |
| 5,224,498 A | 7/1993 | Deevi et al. |
| 5,240,922 A | 8/1993 | O'Neill |
| 5,345,951 A | 9/1994 | Serrano et al. |
| 5,366,770 A | 11/1994 | Wang |
| 5,388,574 A | 2/1995 | Ingebrethsen |
| 5,456,247 A | 10/1995 | Shilling et al. |
| 5,457,100 A | 10/1995 | Daniel |
| 5,511,726 A | 4/1996 | Greenspan et al. |
| 5,543,434 A | 8/1996 | Weg |
| 5,544,646 A | 8/1996 | Lloyd et al. |
| 5,564,442 A | 10/1996 | MacDonald et al. |
| 5,592,934 A | 1/1997 | Thwaites |
| 5,605,146 A | 2/1997 | Sarela |
| 5,607,691 A | 3/1997 | Hale et al. |
| 5,622,944 A | 4/1997 | Hale et al. |
| 5,649,554 A | 7/1997 | Sprinkel |
| 5,655,523 A | 8/1997 | Hodson et al. |
| 5,666,977 A | 9/1997 | Higgins et al. |
| 5,694,919 A | 12/1997 | Rubsamen et al. |
| 5,735,263 A | 4/1998 | Rubsamen et al. |
| 5,738,865 A | 4/1998 | Baichwal et al. |
| 5,743,251 A | 4/1998 | Howell et al. |
| 5,758,637 A | 6/1998 | Ivri et al. |
| 5,767,117 A | 6/1998 | Moskowitz et al. |
| 5,819,756 A | 10/1998 | Mielordt |
| 5,840,246 A | 11/1998 | Hammons et al. |
| 5,855,913 A | 1/1999 | Hanes et al. |
| 5,874,481 A | 2/1999 | Weers et al. |
| 5,894,841 A | 4/1999 | Voges |
| 5,915,378 A | 6/1999 | Lloyd et al. |
| 5,918,595 A | 7/1999 | Olsson |
| 5,934,272 A | 8/1999 | Lloyd et al. |
| 5,957,124 A | 9/1999 | Lloyd et al. |
| 5,960,792 A | 10/1999 | Lloyd et al. |
| 5,993,805 A | 11/1999 | Sutton et al. |
| 6,041,777 A | 3/2000 | Faithfull et al. |
| 6,048,857 A | 4/2000 | Ellinwood, Jr. et al. |
| 6,051,566 A | 4/2000 | Bianco |
| RE36,744 E | 6/2000 | Goldberg |
| 6,090,212 A | 7/2000 | Mahawili |
| 6,095,134 A | 8/2000 | Sievers et al. |
| 6,095,153 A | 8/2000 | Kessler et al. |
| 6,102,036 A | 8/2000 | Slutsky et al. |
| 6,131,570 A | 10/2000 | Schuster et al. |
| 6,136,295 A | 10/2000 | Edwards et al. |
| 6,140,323 A | 10/2000 | Ellinwood, Jr. et al. |
| 6,155,268 A | 12/2000 | Takeuchi |
| 6,158,431 A | 12/2000 | Poole |
| 6,234,167 B1 | 5/2001 | Cox et al. |
| 6,241,969 B1 | 6/2001 | Saidi et al. |
| 6,255,334 B1 | 7/2001 | Sands |
| 6,413,930 B1 | 7/2002 | Ratti et al. |
| 6,461,591 B1 | 10/2002 | Keller et al. |
| 6,506,762 B1 | 1/2003 | Horvath et al. |
| 6,514,482 B1 | 2/2003 | Bartus et al. |
| 6,591,839 B2 | 7/2003 | Meyer et al. |
| 6,632,047 B2 | 10/2003 | Vinegar et al. |
| 6,682,716 B2 | 1/2004 | Hodges et al. |
| 6,701,922 B2 | 3/2004 | Hindle et al. |
| 6,716,415 B2 | 4/2004 | Rabinowitz et al. |
| 6,716,416 B2 | 4/2004 | Rabinowitz et al. |
| 6,716,417 B2 | 4/2004 | Rabinowitz et al. |
| 6,737,042 B2 | 5/2004 | Rabinowitz et al. |
| 6,737,043 B2 | 5/2004 | Rabinowitz et al. |
| 6,740,307 B2 | 5/2004 | Rabinowitz et al. |
| 6,740,308 B2 | 5/2004 | Rabinowitz et al. |
| 6,740,309 B2 | 5/2004 | Rabinowitz et al. |
| 6,743,415 B2 | 6/2004 | Rabinowitz et al. |
| 6,759,029 B2 | 7/2004 | Hale et al. |
| 6,772,756 B2 | 8/2004 | Shayan |
| 6,776,978 B2 | 8/2004 | Rabinowitz et al. |
| 6,780,399 B2 | 8/2004 | Rabinowitz et al. |
| 6,780,400 B2 | 8/2004 | Rabinowitz et al. |
| 6,783,753 B2 | 8/2004 | Rabinowitz et al. |
| 6,797,259 B2 | 9/2004 | Rabinowitz et al. |
| 6,803,031 B2 | 10/2004 | Rabinowitz et al. |
| 6,805,853 B2 | 10/2004 | Rabinowitz et al. |
| 6,805,854 B2 | 10/2004 | Hale et al. |
| 6,814,954 B2 | 11/2004 | Rabinowitz et al. |
| 6,814,955 B2 | 11/2004 | Rabinowitz et al. |
| 6,855,310 B2 | 2/2005 | Rabinowitz et al. |
| 6,884,408 B2 | 4/2005 | Rabinowitz et al. |
| 6,994,843 B2 | 2/2006 | Rabinowitz et al. |
| 7,005,121 B2 | 2/2006 | Rabinowitz et al. |
| 7,005,122 B2 | 2/2006 | Hale et al. |
| 7,008,615 B2 | 3/2006 | Rabinowitz et al. |
| 7,008,616 B2 | 3/2006 | Rabinowitz et al. |
| 7,011,819 B2 | 3/2006 | Hale et al. |
| 7,011,820 B2 | 3/2006 | Rabinowitz et al. |
| 7,014,840 B2 | 3/2006 | Hale et al. |
| 7,014,841 B2 | 3/2006 | Rabinowitz et al. |
| 7,018,619 B2 | 3/2006 | Rabinowitz et al. |
| 7,018,620 B2 | 3/2006 | Rabinowitz et al. |
| 7,018,621 B2 | 3/2006 | Hale et al. |
| 7,022,312 B2 | 4/2006 | Rabinowitz et al. |
| 7,029,658 B2 | 4/2006 | Rabinowitz et al. |
| 7,033,575 B2 | 4/2006 | Rabinowitz et al. |
| 7,045,118 B2 | 5/2006 | Rabinowitz et al. |
| 7,045,119 B2 | 5/2006 | Rabinowitz et al. |
| 7,048,909 B2 | 5/2006 | Rabinowitz et al. |
| 7,052,679 B2 | 5/2006 | Rabinowitz et al. |
| 7,052,680 B2 | 5/2006 | Rabinowitz et al. |
| 7,060,254 B2 | 6/2006 | Rabinowitz et al. |
| 7,060,255 B2 | 6/2006 | Rabinowitz et al. |
| 7,063,830 B2 | 6/2006 | Rabinowitz et al. |
| 7,063,831 B2 | 6/2006 | Rabinowitz et al. |
| 7,063,832 B2 | 6/2006 | Rabinowitz et al. |
| 7,067,114 B2 | 6/2006 | Rabinowitz et al. |
| 7,070,761 B2 | 7/2006 | Rabinowitz et al. |
| 7,070,762 B2 | 7/2006 | Rabinowitz et al. |
| 7,070,763 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,070,766 B2 | 7/2006 | Rabinowitz et al. |
| 7,078,016 B2 | 7/2006 | Rabinowitz et al. |
| 7,078,017 B2 | 7/2006 | Rabinowitz et al. |
| 7,078,018 B2 | 7/2006 | Rabinowitz et al. |
| 7,078,019 B2 | 7/2006 | Rabinowitz et al. |
| 7,078,020 B2 | 7/2006 | Rabinowitz et al. |
| 7,087,216 B2 | 8/2006 | Rabinowitz et al. |
| 7,087,217 B2 | 8/2006 | Rabinowitz et al. |
| 7,087,218 B2 | 8/2006 | Rabinowitz et al. |
| 7,090,830 B2 | 8/2006 | Hale et al. |
| 7,094,392 B2 | 8/2006 | Rabinowitz et al. |
| 7,108,847 B2 | 9/2006 | Rabinowitz et al. |
| 7,115,250 B2 | 10/2006 | Rabinowitz et al. |
| 7,169,378 B2 | 1/2007 | Rabinowitz et al. |
| 7,402,777 B2 | 7/2008 | Ron et al. |
| 7,766,013 B2 * | 8/2010 | Wensley et al. .......... 128/203.27 |
| 2001/0020147 A1 | 9/2001 | Staniforth et al. |
| 2002/0037828 A1 | 3/2002 | Wilson et al. |
| 2002/0058009 A1 | 5/2002 | Bartus et al. |
| 2002/0086852 A1 | 7/2002 | Cantor |
| 2002/0112723 A1 | 8/2002 | Schuster et al. |
| 2002/0117175 A1 | 8/2002 | Kottayil et al. |
| 2002/0176841 A1 | 11/2002 | Barker et al. |
| 2003/0004142 A1 | 1/2003 | Prior et al. |
| 2003/0015196 A1 | 1/2003 | Hodges et al. |
| 2003/0015197 A1 | 1/2003 | Hale et al. |
| 2003/0032638 A1 | 2/2003 | Kim et al. |
| 2003/0051728 A1 | 3/2003 | Lloyd et al. |
| 2003/0062042 A1 | 4/2003 | Wensley et al. |
| 2003/0118512 A1 | 6/2003 | Shen |
| 2003/0131843 A1 | 7/2003 | Lu |
| 2003/0138508 A1 | 7/2003 | Novack et al. |
| 2003/0209240 A1 | 11/2003 | Hale et al. |
| 2004/0009128 A1 | 1/2004 | Rabinowitz et al. |
| 2004/0016427 A1 | 1/2004 | Byron et al. |
| 2004/0096402 A1 | 5/2004 | Hodges et al. |
| 2004/0099266 A1 | 5/2004 | Cross et al. |
| 2004/0101481 A1 | 5/2004 | Hale et al. |
| 2004/0102434 A1 | 5/2004 | Hale et al. |
| 2004/0105818 A1 | 6/2004 | Every et al. |
| 2004/0105819 A1 | 6/2004 | Hale et al. |
| 2004/0234699 A1 | 11/2004 | Hale et al. |
| 2004/0234914 A1 | 11/2004 | Hale et al. |

| | | | |
|---|---|---|---|
| 2004/0234916 | A1 | 11/2004 | Hale et al. |
| 2005/0034723 | A1 | 2/2005 | Bennett et al. |
| 2005/0037506 | A1 | 2/2005 | Hale et al. |
| 2005/0079166 | A1 | 4/2005 | Damani et al. |
| 2005/0126562 | A1 | 6/2005 | Rabinowitz et al. |
| 2005/0131739 | A1 | 6/2005 | Rabinowitz et al. |
| 2005/0268911 | A1 | 12/2005 | Cross et al. |
| 2006/0032496 | A1 | 2/2006 | Hale et al. |
| 2006/0032501 | A1 | 2/2006 | Hale et al. |
| 2006/0120962 | A1 | 6/2006 | Rabinowitz et al. |
| 2006/0153779 | A1 | 7/2006 | Rabinowitz et al. |
| 2006/0177382 | A1 | 8/2006 | Rabinowitz et al. |
| 2006/0193788 | A1 | 8/2006 | Hale et al. |
| 2006/0216243 | A1 | 9/2006 | Rabinowitz et al. |
| 2006/0216244 | A1 | 9/2006 | Rabinowitz et al. |
| 2006/0233717 | A1 | 10/2006 | Hale et al. |
| 2006/0233718 | A1 | 10/2006 | Rabinowitz et al. |
| 2006/0233719 | A1 | 10/2006 | Rabinowitz et al. |
| 2006/0239936 | A1 | 10/2006 | Rabinowitz et al. |
| 2006/0246011 | A1 | 11/2006 | Rabinowitz et al. |
| 2006/0246012 | A1 | 11/2006 | Rabinowitz et al. |
| 2006/0251587 | A1 | 11/2006 | Rabinowitz et al. |
| 2006/0251588 | A1 | 11/2006 | Rabinowitz et al. |
| 2006/0257328 | A1 | 11/2006 | Rabinowitz et al. |
| 2006/0257329 | A1 | 11/2006 | Rabinowitz et al. |
| 2006/0269486 | A1 | 11/2006 | Rabinowitz et al. |
| 2006/0269487 | A1 | 11/2006 | Rabinowitz et al. |
| 2006/0280692 | A1 | 12/2006 | Rabinowitz et al. |
| 2006/0286042 | A1 | 12/2006 | Rabinowitz et al. |
| 2006/0286043 | A1 | 12/2006 | Rabinowitz et al. |
| 2007/0014737 | A1 | 1/2007 | Rabinowitz et al. |
| 2007/0028916 | A1 | 2/2007 | Hale et al. |
| 2007/0031340 | A1 | 2/2007 | Hale et al. |
| 2007/0122353 | A1 | 5/2007 | Hale et al. |
| 2007/0140982 | A1 | 6/2007 | Every et al. |
| 2007/0178052 | A1 | 8/2007 | Rabinowitz et al. |
| 2007/0286816 | A1 | 12/2007 | Hale et al. |
| 2008/0110872 | A1 | 5/2008 | Hale et al. |

FOREIGN PATENT DOCUMENTS

| | | |
|---|---|---|
| EP | 0 358 114 | 3/1990 |
| EP | 0 606 486 | 7/1994 |
| EP | 1 080 720 | 3/2001 |
| GB | 502 761 | 1/1938 |
| WO | WO 85/00520 | 2/1985 |
| WO | WO 90/02737 | 3/1990 |
| WO | WO 94/09842 | 5/1994 |
| WO | WO 96/09846 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 97/16181 | 5/1997 |
| WO | WO 97/27804 | 8/1997 |
| WO | WO 97/36574 | 10/1997 |
| WO | WO 98/22170 | 5/1998 |
| WO | WO 98/31346 | 7/1998 |
| WO | WO 98/36651 | 8/1998 |
| WO | WO 98/37896 | 8/1998 |
| WO | WO 99/16419 | 4/1999 |
| WO | WO 99/64094 | 12/1999 |
| WO | WO 00/00176 | 1/2000 |
| WO | WO 00/00215 | 1/2000 |
| WO | WO 00/27363 | 5/2000 |
| WO | WO 00/28979 | 5/2000 |
| WO | WO 00/29053 | 5/2000 |
| WO | WO 00/47203 | 9/2000 |
| WO | WO 00/64940 | 11/2000 |
| WO | WO 00/66084 | 11/2000 |
| WO | WO 00/66206 | 11/2000 |
| WO | WO 00/76673 | 12/2000 |
| WO | WO 01/05459 | 1/2001 |
| WO | WO 01/41732 | 6/2001 |
| WO | WO 01/95903 | 12/2001 |
| WO | WO 02/00198 | 1/2002 |
| WO | WO 02/24158 | 3/2002 |
| WO | WO 03/037412 | 5/2003 |

OTHER PUBLICATIONS

Office Action mailed Jan. 12, 2005 with respect to U.S. Appl. No. 10/057,197.
Office Action mailed Sep. 21, 2006 with respect to U.S. Appl. No. 10/057,197.
Office Action mailed Feb. 27, 2004 with respect to U.S. Appl. No. 10/146,080.
Office Action mailed Aug. 25, 2005 with respect to U.S. Appl. No. 10/146,080.
Office Action mailed Jun. 5, 2006 with respect to U.S. Appl. No. 10/146,080.
Office Action mailed Mar. 20, 2007 with respect to U.S. Appl. No. 10/146,080.
Office Action mailed Aug. 13, 2003 with respect to U.S. Appl. No. 10/153,313.
Bennett, R. L. et al. (1981). "Patient-Controlled Analgesia: A New Concept of Postoperative Pain Relief," Annual Surg. 195(6):700-705.
Carroll, M.E. et al. (1990), "Cocaine-Base Smoking in Rhesus Monkey: Reinforcing and Physiological Effects," Psychopharmacology (Berl) 102:443-450.
Clark, A. and Byron, P. (1986). "Dependence of Pulmonary Absorption Kinetics on Aerosol Particle Size," Z. Erkrank. 166:13-24.
Darquenne, C. et al. (1997). "Aerosol Dispersion in Human Lung: Comparison Between Numerical Simulations and Experiments for Bolus Tests," American Physiological Society. 966-974.
Davies, C.N. et al. (May 1972). "Breathing of Half-Micron Aerosols," Journal of Applied Physiology. 32(5):591-600.
Dershwitz, M., M.D., et al. (Sep. 2000). "Pharmacokinetics and Pharmacodynamics of Inhaled versus Intravenous Morphine in Healthy Volunteers," Anesthesiology. 93(3): 619-628.
Finlay, W.H. (2001). "The Mechanics of Inhaled Pharmaceutical Aerosols", Academic Press: San Diego Formula 2.39. pp. 3-14 (Table of Contents). pp. v-viii.
Gonda, I. (1991). "Particle Deposition in the Human Respiratory Tract," Chapter 176, The Lung: Scientific Foundations. Crystal R.G. and West, J.B. (eds.), Raven Publishers, New York. pp. 2289-2294.
Hatsukami D, et al. (May 1990) "A method for delivery of precise doses of smoked cocaine-base to humans." Pharmacology Biochemistry & Behavior. 36(1):1-7.
Heyder, J. et al. (1986). "Deposition of Particles in the Human Respiratory Tract in the Size Range 0.005-15 .mu.m," J. Aerosol Sci. 17(5):811-822.
Huizer, H., "Analytical studies on illicit heron. V. Efficacy of volatilization during heroin smoking." Pharmaceutisch Weekblad Scientific Edition (1987). 9(4):203-211.
Hurt, R.D., MD and Robertson, C.R., PhD, (Oct. 1998). "Prying Open the Door to the Tobacco Industry's Secrets About Nicotine: The Minnesota Tobacco Trial," JAMA 280(13):1173-1181.
Lichtman, A.H. et al. (1996). "Inhalation Exposure to Volatilized Opioids Produces Antinociception in Mice," Journal of Pharmacology and Experimental Therapeutics. 279(1):69-76.
Martin, B.R. and Lue, L.P. (May/Jun. 1989). "Pyrolysis and Volatilization of Cocaine," Journal of Analytical Toxicology 13:158-162.
Mattox, A.J. and Carroll, M.E., (1996). "Smoked heroin self-administration in rhesus monkeys," Psychopharmacology, 125:195-201.
Meng, Y. et al. "Inhalation Studies With Drugs of Abuse," NIDA Research Monograph, (1997) 173:201-224.
Meng, Y., et al. (1999). "Pharmacological effects of methamphetamine and other stimulants via inhalation exposure," Drug and Alcohol Dependence. 53:111-120.
Pankow, J. (Mar. 2000). ACS Conference—San Francisco—Mar. 26, 2000. Chemistry of Tobacco Smoke. pp. 1-8.
Pankow, J.F. et al. (1997). "Conversion of Nicotine in Tobacco Smoke to Its Volatile and Available Free-Base Form Through the Action of Gaseous Ammonia," Envron. Sci. Technol. 31:2428-2433.
Seeman, J. et al. (1999). "The Form of Nicotine in Tobacco. Thermal Transfer of Nicotine and Nicotine Acid Salts to Nicotine in the Gas Phase," J. Agric. Food Chem. 47(12):5133-5145.
Sekine, H. and Nakahara, Y. (1987). "Abuse of Smoking Methamphetamine Mixed with Tobacco: 1. Inhalation Efficiency and Pyrolysis Products of Methamphetamine," Journal of Forensic Science 32(5):1271-1280.
Vapotronics, Inc. (1998) located at http://www.vapotronics.com.au/banner.htm., 11 pages, (visited on Jun. 5, 2000).

Ward, M.E. MD, et al. (Dec. 1997). "Morphine Pharmacokinetics after Pulmonary Administration from a Novel Aerosol Delivery System," Clinical Pharmacology & Therapeutics 62(6):596-609.

Wood, R.W. et al. (1996). "Methylecgonidine Coats the Crack Particle" Pharmacology Biochemistry & Behavior. 53(1):57-66.

Wood, R.W. et al. (1996). "Generation of Stable Test Atmospheres of Cocaine Base and Its Pyrolyzate, Methylecgonidine, and Demonstration of Their Biological Activity." Pharmacology Biochemistry & Behavior. 55(2):237-248.

* cited by examiner

DELIVERY OF DRUG ESTERS THROUGH AN INHALATION ROUTE

This application is a continuation of U.S. application Ser. No. 11/488,943, entitled "Delivery of Drug Esters Through an Inhalation Route," filed Jul. 18, 2003, Rabinowitz and Zaffaroni, which is a continuation of U.S. Pat. No. 7,078,019, entitled "Delivery of Drug Esters Through an Inhalation Route," filed Dec. 30, 2003, Rabinowitz and Zaffaroni, which is a continuation of U.S. Pat. No. 6,737,042 entitled "Delivery of Drug Esters Through an Inhalation Route," filed May 13, 2002, Rabinowitz and Zaffaroni, which claims priority to U.S. provisional application Ser. No. 60/294,203 entitled "Thermal Vapor Delivery of Drugs," filed May 24, 2001 and to U.S. provisional application Ser. No. 60/317,479 entitled "Aerosol Drug Delivery," filed Sep. 5, 2001, all of which are hereby incorporated by reference in their entirety.

FIELD OF THE INVENTION

The present invention relates to the delivery of drug esters through an inhalation route. Specifically, it relates to aerosols containing drug esters that are used in inhalation therapy.

BACKGROUND OF THE INVENTION

There are a number of compounds containing acids and alcohols that are currently marketed as drugs. In certain circumstances, the presence of such functionality prevents effective drug delivery. This phenomenon could be due to a range of effects, including poor solubility and inadequate transcellular transport.

It is desirable to provide a new route of administration for drug acids and alcohols that rapidly produces peak plasma concentrations of the compounds. The provision of such a route is an object of the present invention.

SUMMARY OF THE INVENTION

The present invention relates to the delivery of drug esters through an inhalation route. Specifically, it relates to aerosols containing drug esters that are used in inhalation therapy.

In a composition aspect of the present invention, the aerosol comprises particles comprising at least 5 percent by weight of drug ester. Preferably, the drug ester has a decomposition index less than 0.15. More preferably, it has a decomposition index less than 0.10 or 0.05. Preferably, the particles comprise at least 10 percent by weight of drug ester. More preferably, the particles comprise at least 20 percent, 30 percent, 40 percent, 50 percent, 60 percent, 70 percent, 80 percent, 90 percent, 95 percent, 97 percent, 99 percent, 99.5 percent or 99.97 percent by weight of drug ester.

Typically, the drug ester is an ester of a drug from one of the following classes: antibiotics, anticonvulsants, antidepressants, antihistamines, antiparkinsonian drugs, drugs for migraine headaches, drugs for the treatment of alcoholism, muscle relaxants, anxiolytics, nonsteroidal anti-inflammatories, other analgesics and steroids.

Typically, where the drug ester is an ester of an antibiotic, it is selected from an ester of one of the following compounds: cefmetazole; cefazolin; cephalexin; cefoxitin; cephacetrile; cephaloglycin; cephaloridine; cephalosporins, such as cephalosporin c; cephalotin; cephamycins, such as cephamycin a, cephamycin b, and cephamycin c; cepharin; cephradine; ampicillin; amoxicillin; hetacillin; carfecillin; carindacillin; carbenicillin; amylpenicillin; azidocillin; benzylpenicillin; clometocillin; cloxacillin; cyclacillin; methicillin; nafcillin; 2-pentenylpenicillin; penicillins, such as penicillin n, penicillin o, penicillin s, and penicillin v; chlorobutin penicillin; dicloxacillin; diphenicillin; heptylpenicillin; and metampicillin.

Typically, where the drug ester is an ester of an anticonvulsant, it is selected from an ester of one of the following compounds: 4-amino-3-hydroxybutyric acid, ethanedisulfonate, gabapentin, and vigabatrin.

Typically, where the drug ester is an ester of an antidepressant, it is selected from an ester of one of the following compounds: tianeptine and S-adenosylmethionine.

Typically, where the drug ester is an ester of an antihistamine, it is an ester of fexofenadine.

Typically, where the drug ester is an ester of an antiparkinsonian drug, it is selected from an ester of one of the following compounds: apomorphine, baclofen, levodopa, carbidopa, and thioctate.

Typically, where the drug ester is an ester of a drug for migraine headaches, it is selected from an ester of one of the following compounds: aspirin, diclofenac, naproxen, tolfenamic acid, and valproate.

Typically, where the drug ester is an ester of a drug for the treatment of alcoholism, it is an ester of acamprosate.

Typically, where the drug ester is an ester of a muscle relaxant, it is an ester of baclofen.

Typically, where the drug ester is an ester of an anxiolytic, it is selected from an ester of one of the following compounds: chlorazepate, calcium N-carboamoylaspartate and chloral betaine.

Typically, where the drug ester is an ester of a nonsteroidal anti-inflammatory, it is selected from an ester of one of the following compounds: aceclofenac, alclofenac, alminoprofen, amfenac, aspirin, benoxaprofen, bermoprofen, bromfenac, bufexamac, butibufen, bucloxate, carprofen, cinchophen, cinmetacin, clidanac, clopriac, clometacin, diclofenac, diflunisal, etodolac, fenclozate, fenoprofen, flutiazin, flurbiprofen, ibuprofen, ibufenac, indomethacin, indoprofen, ketoprofen, ketorolac, loxoprofen, meclofenamate, naproxen, oxaprozin, pirprofen, prodolic acid, salsalate, sulindac, tofenamate, and tolmetin.

Typically, where the drug ester is an ester of an other analgesic, it is selected from an ester of one of the following compounds: bumadizon, clometacin, and clonixin.

Typically, where the drug ester is an ester of a steroid, it is selected from an ester of one of the following compounds: betamethasone, chloroprednisone, clocortolone, cortisone, desonide, dexamethasone, desoximetasone, difluprednate, estradiol, fludrocortisone, flumethasone, flunisolide, fluocortolone, fluprednisolone, hydrocortisone, meprednisone, methylprednisolone, paramethasone, prednisolone, prednisone, pregnan-3-alpha-ol-20-one, testosterone, and triamcinolone.

Typically, where the drug ester is an ester of a drug acid, the ester is selected from an ester of the following type: $C_1$-$C_6$ straight chain substituted or unsubstituted alkyl ester, $C_1$-$C_6$ branched chain substituted or unsubstituted alkyl ester, $C_3$-$C_6$ substituted or unsubstituted cyclic alkyl ester, $C_1$-$C_6$ substituted or unsubstituted alkenyl ester, $C_1$-$C_6$ substituted or unsubstituted alkynyl ester, and substituted or unsubstituted aromatic ester.

Typically, where the drug ester is an ester of a drug alcohol, the ester is selected from an ester of the following type: $C_1$-$C_6$ substituted or unsubstituted straight chain alkanoate, $C_1$-$C_6$ substituted or unsubstituted branched chain alkanoate, $C_1$-$C_6$ substituted or unsubstituted alkenoate, and $C_1$-$C_6$ substituted or unsubstituted alkynoate.

Typically, the drug ester is selected from one of the following: ketoprofen methyl ester, ketoprofen ethyl ester, ketoprofen norcholine ester, ketorolac methyl ester, ketorolac ethyl ester, ketorolac norcholine ester, indomethacin methyl ester, indomethacin ethyl ester, indomethacine norcholine ester, and apomorphine diacetate.

Typically, the aerosol has a mass of at least 0.01 mg. Preferably, the aerosol has a mass of at least 0.05 mg. More preferably, the aerosol has a mass of at least 0.10 mg, 0.15 mg, 0.2 g or 0.25 mg.

Typically, the particles comprise less than 10 percent by weight of drug ester degradation products. Preferably, the particles comprise less than 5 percent by weight of drug ester degradation products. More preferably, the particles comprise less than 2.5, 1, 0.5, 0.1 or 0.03 percent by weight of drug ester degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, the aerosol has an inhalable aerosol drug ester mass density of between 0.1 mg/L and 100 mg/L. Preferably, the aerosol has an inhalable aerosol drug mass density of between 0.1 mg/L and 75 mg/L. More preferably, the aerosol has an inhalable aerosol drug mass density of between 0.1 mg/L and 50 mg/L.

Typically, the aerosol has an inhalable aerosol particle density greater than $10^6$ particles/mL. Preferably, the aerosol has an inhalable aerosol particle density greater than $10^7$ particles/mL or $10^8$ particles/mL.

Typically, the aerosol particles have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 2. Preferably, the geometric standard deviation is less than 1.9. More preferably, the geometric standard deviation is less than 1.8, 1.7, 1.6 or 1.5.

Typically, the aerosol is formed by heating a composition containing drug ester to form a vapor and subsequently allowing the vapor to condense into an aerosol.

In a method aspect of the present invention, a drug ester is delivered to a mammal through an inhalation route. The method comprises: a) heating a composition, wherein the composition comprises at least 5 percent by weight of drug ester, to form a vapor; and, b) allowing the vapor to cool, thereby forming a condensation aerosol comprising particles, which is inhaled by the mammal. Preferably, the drug ester has a decomposition index less than 0.15. More preferably, it has a decomposition index less than 0.10 or 0.05. Preferably, the composition that is heated comprises at least 10 percent by weight of drug ester. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of drug ester.

Typically, the drug ester is an ester of a drug from one of the following classes: antibiotics, anticonvulsants, antidepressants, antihistamines, antiparkinsonian drugs, drugs for migraine headaches, drugs for the treatment of alcoholism, muscle relaxants, anxiolytics, nonsteroidal anti-inflammatories, other analgesics and steroids.

Typically, where the drug ester is an ester of an antibiotic, it is selected from an ester of one of the following compounds: cefmetazole; cefazolin; cephalexin; cefoxitin; cephacetrile; cephaloglycin; cephaloridine; cephalosporins, such as cephalosporin c; cephalotin; cephamycins, such as cephamycin a, cephamycin b, and cephamycin c; cepharin; cephradine; ampicillin; amoxicillin; hetacillin; carfecillin; carindacillin; carbenicillin; amylpenicillin; azidocillin; benzylpenicillin; clometocillin; cloxacillin; cyclacillin; methicillin; nafcillin; 2-pentenylpenicillin; penicillins, such as penicillin n, penicillin o, penicillin s, and penicillin v; chlorobutin penicillin; dicloxacillin; diphenicillin; heptylpenicillin; and metampicillin.

Typically, where the drug ester is an ester of an anticonvulsant, it is selected from an ester of one of the following compounds: 4-amino-3-hydroxybutyric acid, ethanedisulfonate, gabapentin, and vigabatrin.

Typically, where the drug ester is an ester of an antidepressant, it is selected from an ester of one of the following compounds: tianeptine and S-adenosylmethionine.

Typically, where the drug ester is an ester of an antihistamine, it is an ester of fexofenadine.

Typically, where the drug ester is an ester of an antiparkinsonian drug, it is selected from an ester of one of the following compounds: apomorphine, baclofen, levodopa, carbidopa, and thioctate.

Typically, where the drug ester is an ester of a drug for migraine headaches, it is selected from an ester of one of the following compounds: aspirin, diclofenac, naproxen, tolfenamic acid, and valproate.

Typically, where the drug ester is an ester of a drug for the treatment of alcoholism, it is an ester of acamprosate.

Typically, where the drug ester is an ester of a muscle relaxant, it is an ester of baclofen.

Typically, where the drug ester is an ester of an anxiolytic, it is selected from an ester of one of the following compounds: chlorazepate, calcium N-carboamoylaspartate and chloral betaine.

Typically, where the drug ester is an ester of a nonsteroidal anti-inflammatory, it is selected from an ester of one of the following compounds: aceclofenac, alclofenac, alminoprofen, amfenac, aspirin, benoxaprofen, bermoprofen, bromfenac, bufexamac, butibufen, bucloxate, carprofen, cinchophen, cinmetacin, clidanac, clopriac, clometacin, diclofenac, diflunisal, etodolac, fenclozate, fenoprofen, flutiazin, flurbiprofen, ibuprofen, ibufenac, indomethacin, indoprofen, ketoprofen, ketorolac, loxoprofen, meclofenamate, naproxen, oxaprozin, pirprofen, prodolic acid, salsalate, sulindac, tofenamate, and tolmetin.

Typically, where the drug ester is an ester of an other analgesic, it is selected from an ester of one of the following compounds: bumadizon, clometacin, and clonixin.

Typically, where the drug ester is an ester of a steroid, it is selected from an ester of one of the following compounds: betamethasone, chloroprednisone, clocortolone, cortisone, desonide, dexamethasone, desoximetasone, difluprednate, estradiol, fludrocortisone, flumethasone, flunisolide, fluocortolone, fluprednisolone, hydrocortisone, meprednisone, methylprednisolone, paramethasone, prednisolone, prednisone, pregnan-3-alpha-ol-20-one, testosterone, and triamcinolone.

Typically, where the drug ester is an ester of a drug acid, the ester is selected from an ester of the following type: $C_1$-$C_6$ straight chain substituted or unsubstituted alkyl ester, $C_1$-$C_6$ branched chain substituted or unsubstituted alkyl ester, $C_3$-$C_6$ substituted or unsubstituted cyclic alkyl ester, $C_1$-$C_6$ substituted or unsubstituted alkenyl ester, $C_1$-$C_6$ substituted or unsubstituted alkynyl ester, and substituted or unsubstituted aromatic ester.

Typically, where the drug ester is an ester of a drug alcohol, the ester is selected from an ester of the following type: $C_1$-$C_6$ substituted or unsubstituted straight chain alkanoate, $C_1$-$C_6$ substituted or unsubstituted branched chain alkanoate, $C_1$-$C_6$ substituted or unsubstituted alkenoate, and $C_1$-$C_6$ substituted or unsubstituted alkynoate.

Typically, the drug ester is selected from one of the following: ketoprofen methyl ester, ketoprofen ethyl ester, ketoprofen norcholine ester, ketorolac methyl ester, ketorolac ethyl ester, ketorolac norcholine ester, indomethacin methyl ester, indomethacin ethyl ester, indomethacine norcholine ester, and apomorphine diacetate.

Typically, the particles comprise at least 5 percent by weight of drug ester. Preferably, the particles comprise at least 10 percent by weight of drug ester. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of drug ester.

Typically, the condensation aerosol has a mass of at least 0.01 mg. Preferably, the aerosol has a mass of at least 0.05 mg. More preferably, the aerosol has a mass of at least 0.10 mg, 0.15 mg, 0.2 g or 0.25 mg.

Typically, the particles comprise less than 10 percent by weight of drug ester degradation products. Preferably, the particles comprise less than 5 percent by weight of drug ester degradation products. More preferably, the particles comprise 2.5, 1, 0.5, 0.1 or 0.03 percent by weight of drug ester degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, the particles of the delivered condensation aerosol have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 2. Preferably, the geometric standard deviation is less than 1.9. More preferably, the geometric standard deviation is less than 1.8, 1.7, 1.6 or 1.5.

Typically, the delivered aerosol has an inhalable aerosol drug ester mass density of between 0.1 mg/L and 100 mg/L. Preferably, the aerosol has an inhalable aerosol drug mass density of between 0.1 mg/L and 75 mg/L. More preferably, the aerosol has an inhalable aerosol drug mass density of between 0.1 mg/L and 50 mg/L.

Typically, the delivered aerosol has an inhalable aerosol particle density greater than $10^6$ particles/mL. Preferably, the aerosol has an inhalable aerosol particle density greater than $10^7$ particles/mL or $10^8$ particles/mL.

Typically, the rate of inhalable aerosol particle formation of the delivered condensation aerosol is greater than $10^8$ particles per second. Preferably, the aerosol is formed at a rate greater than $10^9$ inhalable particles per second. More preferably, the aerosol is formed at a rate greater than $10^{10}$ inhalable particles per second.

Typically, the delivered condensation aerosol is formed at a rate greater than 0.5 mg/second. Preferably, the aerosol is formed at a rate greater than 0.75 mg/second. More preferably, the aerosol is formed at a rate greater than 1 mg/second, 1.5 mg/second or 2 mg/second.

Typically, between 0.1 mg and 100 mg of drug ester are delivered to the mammal in a single inspiration. Preferably, between 0.1 mg and 75 mg of drug ester are delivered to the mammal in a single inspiration. More preferably, between 0.1 mg and 50 mg of drug ester are delivered in a single inspiration.

Typically, the delivered condensation aerosol results in a peak plasma concentration of drug acid or drug alcohol in the mammal in less than 1 h. Preferably, the peak plasma concentration is reached in less than 0.5 h. More preferably, the peak plasma concentration is reached in less than 0.2, 0.1, 0.05, 0.02 or 0.01 h.

In a kit aspect of the present invention, a kit for delivering a drug ester through an inhalation route to a mammal is provided which comprises: a) a composition comprising at least 5 percent by weight of drug ester; and, b) a device that forms a drug ester aerosol from the composition, for inhalation by the mammal. Preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of drug ester.

Typically the drug ester has a decomposition index less than 0.15. More preferably, it has a decomposition index less than 0.10 or 0.05.

Typically, the device contained in the kit comprises: a) an element for heating the drug ester composition to form a vapor; b) an element allowing the vapor to cool to form an aerosol; and, c) an element permitting the mammal to inhale the aerosol.

DETAILED DESCRIPTION OF THE INVENTION

Definitions

Figure 1:
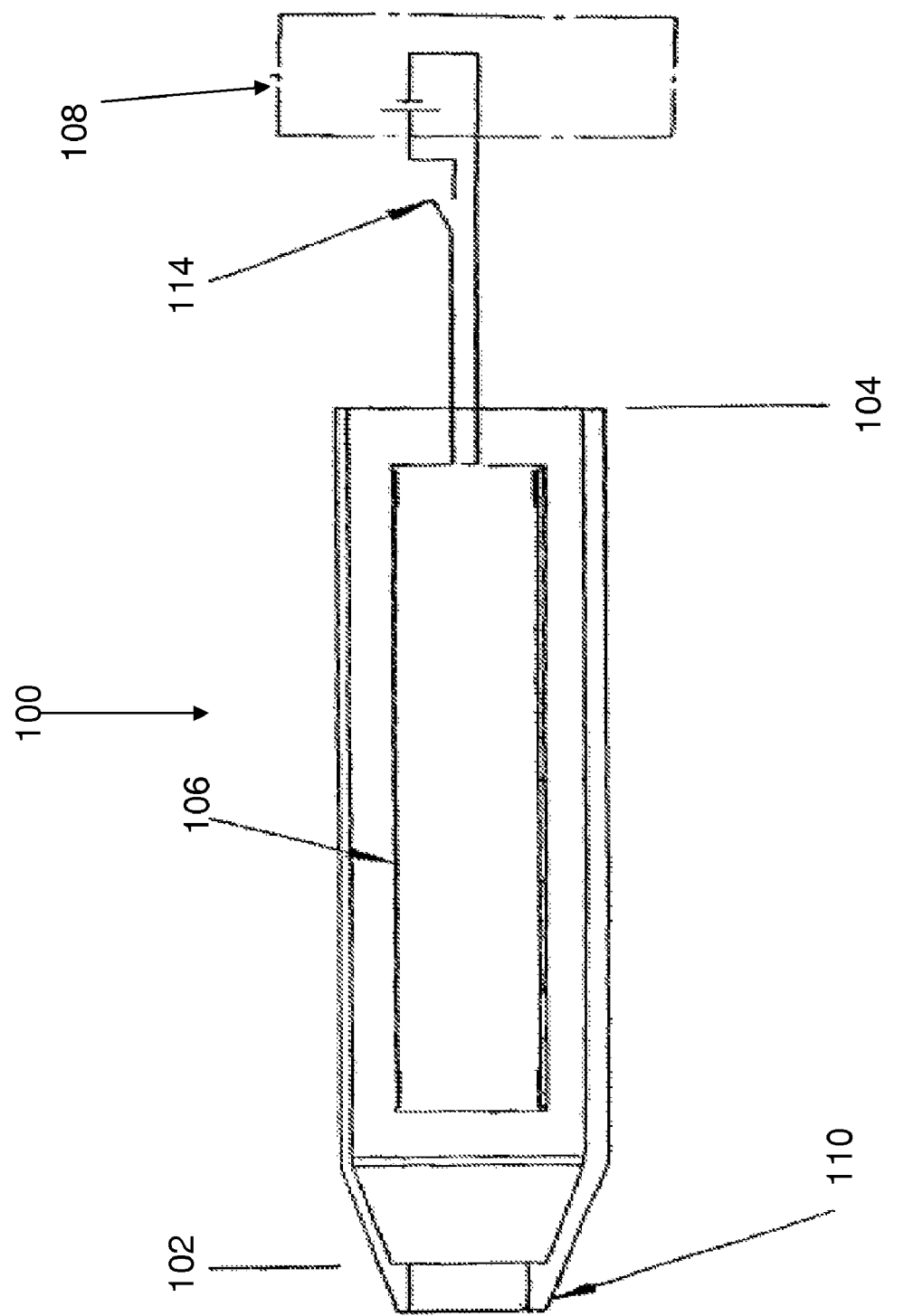
FIG. 1 shows a cross-sectional view of a device used to deliver drug ester aerosols to a mammal through an inhalation route.

"Aerodynamic diameter" of a given particle refers to the diameter of a spherical droplet with a density of 1 g/mL (the density of water) that has the same settling velocity as the given particle.

"Aerosol" refers to a suspension of solid or liquid particles in a gas.

"Aerosol drug ester mass density" refers to the mass of drug ester per unit volume of aerosol.

"Aerosol mass density" refers to the mass of particulate matter per unit volume of aerosol.

"Aerosol particle density" refers to the number of particles per unit volume of aerosol.

"Condensation aerosol" refers to an aerosol formed by vaporization of a substance followed by condensation of the substance into an aerosol.

"Decomposition index" refers to a number derived from an assay described in Example 8. The number is determined by subtracting the percent purity of the generated aerosol from 1.

"Drug" refers to any chemical compound that is used in the prevention, diagnosis, treatment, or cure of disease, for the relief of pain, or to control or improve any physiological or pathological disorder in humans or animals. Such compounds are oftentimes listed in the Physician's Desk Reference (Medical Economics Company, Inc. at Montvale, N.J., 56$^{th}$ edition, 2002), which is herein incorporated by reference.

"Drug acid" refers to a drug containing a carboxylic acid moiety.

"Drug alcohol" refers to a drug containing a hydroxyl moiety.

"Drug Ester" refers to a drug acid or drug alcohol, where the carboxylic acid group or hydroxyl group has been chemically modified to form an ester. The drug acids and alcohols from which the esters are formed come from a variety of drug classes, including, without limitation, antibiotics, anticonvulsants, antidepressants, antihistamines, antiparkinsonian drugs, drugs for migraine headaches, drugs for the treatment of alcoholism, muscle relaxants, anxiolytics, nonsteroidal anti-inflammatories, other analgesics, and steroids.

Examples of antibiotics from which drug esters are formed include cefmetazole; cefazolin; cephalexin; cefoxitin; cephacetrile; cephaloglycin; cephaloridine; cephalosporins, such as cephalosporin c; cephalotin; cephamycins, such as cephamycin a, cephamycin b, and cephamycin c; cepharin; cephradine; ampicillin; amoxicillin; hetacillin; carfecillin; carindacillin; carbenicillin; amylpenicillin; azidocillin; benzylpenicillin; clometocillin; cloxacillin; cyclacillin; methicillin; nafcillin; 2-pentenylpenicillin; penicillins, such as penicillin n, penicillin o, penicillin s, and penicillin v; chlorobutin penicillin; dicloxacillin; diphenicillin; heptylpenicillin; and metampicillin.

Examples of anticonvulsants from which drug esters are formed include 4-amino-3-hydroxybutyric acid, ethanedisulfonate, gabapentin, and vigabatrin.

Examples of antidepressants from which drug esters are formed include tianeptine and S-adenosylmethionine.

Examples of antihistamines from which drug esters are formed include fexofenadine.

Examples of antiparkinsonian drugs from which drug esters are formed include apomorphine, baclofen, levodopa, carbidopa, and thioctate.

Examples of anxiolytics from which drug esters are formed include chlorazepate, calcium N-carboamoylaspartate and chloral betaine.

Examples of drugs for migraine headache from which drug esters are formed include aspirin, diclofenac, naproxen, tolfenamic acid, and valproate.

Examples of drugs for the treatment of alcoholism from which drug esters are formed include acamprosate.

Examples of muscle relaxants from which drug esters are formed include baclofen.

Examples of nonsteroidal anti-inflammatories from which drug esters are formed include aceclofenac, alclofenac, alminoprofen, amfenac, aspirin, benoxaprofen, bermoprofen, bromfenac, bufexamac, butibufen, bucloxate, carprofen, cinchophen, cinmetacin, clidanac, clopriac, clometacin, diclofenac, diflunisal, etodolac, fenclozate, fenoprofen, flutiazin, flurbiprofen, ibuprofen, ibufenac, indomethacin, indoprofen, ketoprofen, ketorolac, loxoprofen, meclofenamate, naproxen, oxaprozin, pirprofen, prodolic acid, salsalate, sulindac, tofenamate, and tolmetin.

Examples of other analgesics from which drug esters are formed include bumadizon, clometacin, and clonixin.

Examples of steroids from which drug esters are formed include betamethasone, chloroprednisone, clocortolone, cortisone, desonide, dexamethasone, desoximetasone, difluprednate, estradiol, fludrocortisone, flumethasone, flunisolide, fluocortolone, fluprednisolone, hydrocortisone, meprednisone, methylprednisolone, paramethasone, prednisolone, prednisone, pregnan-3-alpha-ol-20-one, testosterone, and triamcinolone.

Examples of drug esters formed from drug acids include $C_1$-$C_6$ straight chain substituted or unsubstituted alkyl esters, $C_1$-$C_6$ branched chain substituted or unsubstituted alkyl esters, $C_3$-$C_6$ substituted or unsubstituted cyclic alkyl esters, $C_1$-$C_6$ substituted or unsubstituted alkenyl esters, $C_1$-$C_6$ substituted or unsubstituted alkynyl esters, and substituted or unsubstituted aromatic esters. $C_1$-$C_6$ straight chain unsubstituted alkyl esters include, for example, methyl ester, ethyl ester and propyl ester. $C_1$-$C_6$ straight chain substituted alkyl esters include, for example, 2-(dimethylamino)-ethyl ester (—$CH_2CH_2N(CH_3)_2$). $C_1$-$C_6$ branched chain unsubstituted alkyl esters include, for example, isopropyl ester and isobutyl ester. $C_1$-$C_6$ branched chain substituted alkyl esters include, for example, 2-(dimethylamino)-isopropyl ester (—$CH(CH_3)CH_2N(CH_3)_2$). $C_3$-$C_6$ unsubstituted cyclic alkyl esters include, for example, cyclopropyl and cyclohexyl ester. $C_3$-$C_6$ substituted cyclic alkyl esters include, for example, 2-(dimethylamino)-cyclopropyl ester. $C_1$-$C_6$ unsubstituted alkenyl esters include, for example, 2-butenyl ester (—$CH_2CHCHCH_3$). $C_1$-$C_6$ substituted alkenyl esters include, for example, 4-(dimethylamino)-2-butenyl ester (—$CH_2CHCHCH_2N(CH_3)_2$). $C_1$-$C_6$ unsubstituted alkynyl esters include, for example, 2-butynyl ester (—$CH_2CCCH_3$). $C_1$-$C_6$ substituted alkynyl esters include, for example, 4-(dimethylamino)-2-butynyl ester (—$CH_2CCCH_2N(CH_3)_2$). Unsubstituted aromatic esters include, for example, phenyl ester and naphthyl ester. Substituted aromatic esters include, for example, 4-(dimethylamino)phenyl ester.

Examples of drug esters formed from drug alcohols include $C_1$-$C_6$ substituted or unsubstituted straight chain alkanoates, $C_1$-$C_6$ substituted or unsubstituted branched chain alkanoates, $C_1$-$C_6$ substituted or unsubstituted alkenoates, and $C_1$-$C_6$ substituted or unsubstituted alkynoates. $C_1$-$C_6$ unsubstituted straight chain alkanoates include, for example, methanoate (—C(O)H), ethanoate (—C(O)$CH_3$) and propanoate (—C(O)$CH_2CH_3$). $C_1$-$C_6$ substituted straight chain alkanoates include, for example, 2-(phenyl)-ethanoate (—C(O)$CH_2$Ph). $C_1$-$C_6$ unsubstituted branched chain alkanoates include, for example, isobutanoate (—C(O)CH($CH_3$)$_2$). $C_1$-$C_6$ substituted branched chain alkanoates include, for example, 3-(phenyl)-isobutanoate (—C(O)CH($CH_3$)$CH_2$Ph). $C_1$-$C_6$ unsubstituted alkenoates include, for example, 2-butenoate (—C(O)CHCH$CH_3$). $C_1$-$C_6$ substituted alkenoates include, for example, 4-(phenyl)-2-butenoate (—C(O)CHCHCH$_2$Ph). $C_1$-$C_6$ unsubstituted alkynoates include, for example, 2-butynoate (—C(O)CCCH$_3$). $C_1$-$C_6$ substituted alkynoates include, for example, 4-(phenyl)-2-butynoate.

Examples of other drug esters are found in U.S. Pat. No. 5,607,691 to Hale et al. and U.S. Pat. No. 5,622,944 to Hale et al. These patents are herein incorporated by reference.

"Drug ester degradation product" refers to a compound resulting from a chemical modification of the drug ester. The modification, for example, can be the result of a thermally or photochemically induced reaction. Such reactions include, without limitation, oxidation and hydrolysis.

"Inhalable aerosol drug ester mass density" refers to the aerosol drug ester mass density produced by an inhalation device and delivered into a typical patient tidal volume.

"Inhalable aerosol mass density" refers to the aerosol mass density produced by an inhalation device and delivered into a typical patient tidal volume.

"Inhalable aerosol particle density" refers to the aerosol particle density of particles of size between 100 nm and 5 microns produced by an inhalation device and delivered into a typical patient tidal volume.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Norcholine ester" refers to an ester where the portion attached to the ester oxygen is —$CH_2CH_2N(CH_3)_2$.

"Rate of aerosol formation" refers to the mass of aerosolized particulate matter produced by an inhalation device per unit time.

"Rate of inhalable aerosol particle formation" refers to the number of particles of size between 100 nm and 5 microns produced by an inhalation device per unit time.

"Rate of drug ester aerosol formation" refers to the mass of aerosolized, drug ester produced by an inhalation device per unit time.

"Settling velocity" refers to the terminal velocity of an aerosol particle undergoing gravitational settling in air.

"Substituted" alkyl, alkenyl, alkynyl or aryl refers to the replacement of one or more hydrogen atoms on the moiety (e.g., alkyl) with another group. Such groups include, without limitation, the following: halo, amino, alkylamino, dialkylamino, hydroxyl, cyano, nitro and phenyl.

"Typical patient tidal volume" refers to 1 L for an adult patient and 15 mL/kg for a pediatric patient.

"Vapor" refers to a gas, and "vapor phase" refers to a gas phase. The term "thermal vapor" refers to a vapor phase, aerosol, or mixture of aerosol-vapor phases, formed preferably by heating.

Formation of Drug Esters from Drug Acids or Drug Alcohols

Formation of drug esters from drug acids is typically accomplished by reacting the acid, or an activated derivative (e.g., acid chloride or mixed anhydride) with an appropriate alcohol under conditions well known to those of skill in the art. See, for example, Streitweiser, A., Jr. and Heathcock, C. H. (1981) *Introduction to Organic Chemistry*, Macmillan Publishing Col., Inc., New York. Conversely, formation of drug esters from drug alcohols is typically accomplished by reacting the alcohol with an appropriate activated acid derivative (e.g., ClC(O)$CH_3$). See Id.

Formation of Drug Ester Containing Aerosols

Any suitable method is used to form the aerosols of the present invention. A preferred method, however, involves heating a composition comprising a drug ester to form a vapor, followed by cooling of the vapor such that it condenses to provide a drug ester comprising aerosol (condensation aerosol). The composition is heated in one of two forms: as pure active compound (i.e., pure drug ester); or, as a mixture of active compound and a pharmaceutically acceptable excipient.

Pharmaceutically acceptable excipients may be volatile or nonvolatile. Volatile excipients, when heated, are concurrently volatilized, aerosolized and inhaled with drug ester. Classes of such excipients are known in the art and include, without limitation, gaseous, supercritical fluid, liquid and solid solvents. The following is a list of exemplary carriers within the classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof.

Solid supports on which the composition is heated are of a variety of shapes. Examples of such shapes include, without limitation, cylinders of less than 1.0 mm in diameter, boxes of less than 1.0 mm thickness and virtually any shape permeated by small (e.g., less than 1.0 mm-sized) pores. Preferably, solid supports provide a large surface to volume ratio (e.g., greater than 100 per meter) and a large surface to mass ratio (e.g., greater than 1 $cm^2$ per gram).

A solid support of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials are used to construct the solid supports. Classes of such materials include, without limitation, metals, inorganic materials, carbonaceous materials and polymers. The following are examples of the material classes: aluminum, silver, gold, stainless steel, copper and tungsten; silica, glass, silicon and alumina; graphite, porous carbons, carbon yarns and carbon felts; polytetrafluoroethylene and polyethylene glycol. Combinations of materials and coated variants of materials are used as well.

Where aluminum is used as a solid support, aluminum foil is a suitable material. Examples of silica, alumina and silicon based materials include amphorous silica S-5631 (Sigma, St. Louis, Mo.), BCR171 (an alumina of defined surface area greater than 2 $m^2$/g from Aldrich, St. Louis, Mo.) and a silicon wafer as used in the semiconductor industry. Carbon yarns and felts are available from American Kynol, Inc., New York, N.Y. Chromatography resins such as octadecycl silane chemically bonded to porous silica are exemplary coated variants of silica.

The heating of the drug ester compositions is performed using any suitable method. Examples of methods by which heat can be generated include the following: passage of current through an electrical resistance element; absorption of electromagnetic radiation, such as microwave or laser light; and, exothermic chemical reactions, such as exothermic solvation, hydration of pyrophoric materials and oxidation of combustible materials.

Delivery of Drug Ester Containing Aerosols

Drug ester containing aerosols of the present invention are delivered to a mammal using an inhalation device. Where the aerosol is a condensation aerosol, the device has at least three elements: an element for heating a drug ester containing composition to form a vapor; an element allowing the vapor to cool, thereby providing a condensation aerosol; and, an element permitting the mammal to inhale the aerosol. Various suitable heating methods are described above. The element that allows cooling is, in it simplest form, an inert passageway linking the heating means to the inhalation means. The element permitting inhalation is an aerosol exit portal that forms a connection between the cooling element and the mammal's respiratory system.

One device used to deliver the drug ester containing aerosol is described in reference to FIG. 1. Delivery device 100 has a proximal end 102 and a distal end 104, a heating module 106, a power source 108, and a mouthpiece 110. A drug ester composition is deposited on a surface 112 of heating module 106. Upon activation of a user activated switch 114, power source 108 initiates heating of heating module 106 (e.g, through ignition of combustible fuel or passage of current through a resistive heating element). The drug ester composition volatilizes due to the heating of heating module 106 and condenses to form a condensation aerosol prior to reaching the mouthpiece 110 at the proximal end of the device 102. Air flow traveling from the device distal end 104 to the mouthpiece 110 carries the condensation aerosol to the mouthpiece 110, where it is inhaled by the mammal.

Devices, if desired, contain a variety of components to facilitate the delivery of drug ester containing aerosols. For instance, the device may include any component known in the art to control the timing of drug aerosolization relative to inhalation (e.g., breath-actuation), to provide feedback to patients on the rate and/or volume of inhalation, to prevent excessive use (i.e., "lock-out" feature), to prevent use by unauthorized individuals, and/or to record dosing histories.

In Vivo Hydrolysis of Drug Esters

After delivery of a drug ester aerosol to the lung of an animal, the ester moiety is typically hydrolyzed to provide the corresponding drug acid or drug alcohol, which produces a desired therapeutic effect. Where the ester reacts with water at ~pH 7.4 at an appreciable rate, hydrolysis is chemically mediated. For other esters, hydrolysis is enzymatically mediated through the action of enzymes endogenous to the animal.

Dosage of Drug Ester Containing Aerosols

A typical dosage of a drug ester aerosol is either administered as a single inhalation or as a series of inhalations taken within an hour or less (dosage equals sum of inhaled amounts). Where the drug ester is administered as a series of inhalations, a different amount may be delivered in each inhalation. The dosage amount of drug ester in aerosol form is generally no greater than twice the standard dose of the drug acid or drug alcohol given orally.

One can determine the appropriate dose of drug ester containing aerosols to treat a particular condition using methods such as animal experiments and a dose-finding (Phase I/II) clinical trial. One animal experiment involves measuring plasma concentrations of drug acid or drug alcohol in an animal after its exposure to the aerosol. Mammals such as dogs or primates are typically used in such studies, since their respiratory systems are similar to that of a human. Initial dose levels for testing in humans is generally less than or equal to the dose in the mammal model that resulted in plasma drug levels associated with a therapeutic effect in humans. Dose escalation in humans is then performed, until either an optimal therapeutic response is obtained or a dose-limiting toxicity is encountered.

Analysis of Drug Ester Containing Aerosols

Purity of a drug ester containing aerosol is determined using a number of methods, examples of which are described in Sekine et al., *Journal of Forensic Science* 32:1271-1280 (1987) and Martin et al., *Journal of Analytic Toxicology* 13:158-162 (1989). One method involves forming the aerosol in a device through which a gas flow (e.g., air flow) is maintained, generally at a rate between 0.4 and 60 L/min. The gas flow carries the aerosol into one or more traps. After isolation from the trap, the aerosol is subjected to an analytical technique, such as gas or liquid chromatography, that permits a determination of composition purity.

A variety of different traps are used for aerosol collection. The following list contains examples of such traps: filters; glass wool; impingers; solvent traps, such as dry ice-cooled ethanol, methanol, acetone and dichloromethane traps at various pH values; syringes that sample the aerosol; empty, low-pressure (e.g., vacuum) containers into which the aerosol is drawn; and, empty containers that fully surround and enclose the aerosol generating device. Where a solid such as glass wool is used, it is typically extracted with a solvent such as ethanol. The solvent extract is subjected to analysis rather than the solid (i.e., glass wool) itself. Where a syringe or container is used, the container is similarly extracted with a solvent.

The gas or liquid chromatograph discussed above contains a detection system (i.e., detector). Such detection systems are well known in the art and include, for example, flame ionization, photon absorption and mass spectrometry detectors. An advantage of a mass spectrometry detector is that it can be used to determine the structure of drug ester degradation products.

Particle size distribution of a drug ester containing aerosol is determined using any suitable method in the art (e.g., cascade impaction). An Andersen Eight Stage Non-viable Cascade Impactor (Andersen Instruments, Smyrna, Ga.) linked to a furnace tube by a mock throat (USP throat, Andersen Instruments, Smyrna, Ga.) is one system used for cascade impaction studies.

Inhalable aerosol mass density is determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the tidal volume of an inhaling patient.

Inhalable aerosol drug ester mass density is determined, for example, by delivering a drug ester-containing aerosol into a confined chamber via an inhalation device and measuring the amount of non-degraded drug ester collected in the chamber. Typically, the aerosol is drawn into the chamber by having a pressure gradient between the device and the chamber, wherein the chamber is at lower pressure than the device. The volume of the chamber should approximate the tidal volume of an inhaling patient. The amount of non-degraded drug ester collected in the chamber is determined by extracting the chamber, conducting chromatographic analysis of the extract and comparing the results of the chromatographic analysis to those of a standard containing known amounts of drug ester.

Inhalable aerosol particle density is determined, for example, by delivering aerosol phase drug ester into a confined chamber via an inhalation device and measuring the number of particles of given size collected in the chamber. The number of particles of a given size may be directly measured based on the light-scattering properties of the particles. Alternatively, the number of particles of a given size is determined by measuring the mass of particles within the given size range and calculating the number of particles based on the mass as follows: Total number of particles=Sum (from size range 1 to size range N) of number of particles in each size range. Number of particles in a given size range=Mass in the size range/Mass of a typical particle in the size range. Mass of a typical particle in a given size range=$\pi * D^3 \phi/6$, where D is a typical particle diameter in the size range (generally, the mean boundary MMADs defining the size range) in microns, $\phi$ is the particle density (in g/mL) and mass is given in units of picograms ($g^{-12}$).

Rate of inhalable aerosol particle formation is determined, for example, by delivering aerosol phase drug ester into a confined chamber via an inhalation device. The delivery is for a set period of time (e.g., 3 s), and the number of particles of a given size collected in the chamber is determined as outlined above. The rate of particle formation is equal to the number of 100 nm to 5 micron particles collected divided by the duration of the collection time.

Rate of aerosol formation is determined, for example, by delivering aerosol phase drug ester into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug ester aerosol formation is determined, for example, by delivering a drug ester containing aerosol into a confined chamber via an inhalation device over a set period of time (e.g., 3 s). Where the aerosol is pure drug ester, the amount of drug collected in the chamber is measured as described above. The rate of drug ester aerosol formation is equal to the amount of drug ester aerosol collected in the chamber divided by the duration of the collection time. Where the drug ester containing aerosol comprises a pharmaceutically acceptable excipient, multiplying the rate of aerosol formation by the percentage of drug ester in the aerosol provides the rate of drug aerosol formation.

Utility of Drug Ester Containing Aerosols

The drug ester containing aerosols of the present invention are typically used for the same indication as the corresponding drug acid or drug alcohol. For instance, a drug ester of baclofen would be used to treat parkinsons disease and a drug ester of fexofenadine would be used to treat allergy symptoms.

The following examples are meant to illustrate, rather than limit, the present invention.

Drug acids or drug alcohols are typically commercially available from Sigma, obtained in tablet form from a pharmacy and extracted, or synthesized using well known methods in the art.

EXAMPLE 1

General Procedures for Esterifying a Drug Acid

Drug acid (10 mmol) is dissolved in 90 mL of dichloromethane. To the solution is added 1 drop of dimethylformamide and 13 mmol of oxalyl chloride. The resulting mixture is allowed to stir 30 min. The mixture is concentrated to dryness on a rotary evaporator to provide a residue, to which 50 mL of an alcohol (e.g., methanol) is added. The alcoholic solution is concentrated to dryness to afford the desired drug ester.

Drug acid (6 mmol) is dissolved in 60 mL of dichloromethane. To the solution is added 1 drop of dimethylformamide and 9 mmol of oxalyl chloride. The resulting mixture is allowed to stir 1 h. The mixture is concentrated to dryness on a rotary evaporator to provide a residue, to which 47 mmol of an alcohol (e.g., $HOCH_2CH_2N(CH_3)_2$) in 20 mL dichloromethane is added. The reaction mixture is diluted with 60 mL dichloromethane and subjected to a series of washings: 50 mL saturated aqueous NaCl followed by 50 mL saturated aqueous $NaHCO_3$ and 2×50 mL saturated aqueous NaCl. The dichloromethane extract is dried over $Na_2SO_4$, filtered, and concentrated on a rotary evaporator to provide the desired drug ester.

EXAMPLE 2

General Procedure for Esterifying a Drug Alcohol

Drug alcohol (5 mmol) is dissolved in 50 mL of dichloromethane. To the solution is added 5.5 mmol Hünig's base and 10 mmol acetyl chloride. The reaction mixture is allowed to stir at room temperature for 1 hour. The mixture is washed with 50 mL saturated aqueous $NaHCO_3$ followed by 50 mL saturated aqueous NaCl. The dichloromethane extract is dried over $Na_2SO_4$, filtered, and concentrated on a rotary evaporator to provide the desired drug ester.

EXAMPLE 3

Procedure for Diesterifying Apomorphine

Apomorphine HCl.½$H_2O$ (300 mg) was suspended in 600 µL of acetic acid. The suspension was heated to 100° C. and then cooled to 50° C. Acetyl chloride (1 mL) was added to the suspension, which was heated at 40° C. for 3 h. The reaction mixture was allowed to cool to room temperature. Dichloromethane (1-2 mL) was added and the mixture was allowed to stir overnight. The reaction mixture was diluted with dichloromethane, and the solvent was removed on a rotary evaporator. Toluene (10 mL) was added to the residue and subsequently removed on a rotary evaporator. The toluene addition/removal was repeated. The resulting solid residue was triturated with ether, providing 430 mg of a solid (mp 158-160° C.).

A portion of the solid (230 mg) was suspended in 50 mL of dichloromethane. The suspension was washed with saturated aqueous $NaHCO_3$. The dichloromethane layer was dried over $Na_2SO_4$, filtered and concentrated on a rotary evaporator to provide 190 mg of the desired free base (mp ~110° C.).

EXAMPLE 4

Procedure for Synthesis of 2-(N,N-Dimethylamino)Ethyl Ester of Ketorolac

Ketorolac (255 mg), triethylamine (101 mg) and 2-(dimethylamino)ethanol ($HOCH_2CH_2N(CH_3)_2$, 380 mg) were added to 2 mL dichloromethane. The mixture was cooled to −25° C. to −20° C. for 15 min. BOP (464 mg) was added, and the reaction mixture was gradually allowed to warm to room temperature. See Kim, M. H. and Patel, D. V. (1994) *Tet. Lett.* 35: 5603-5606. The reaction mixture was diluted with 60 mL of dichloromethane and washed sequentially with saturated aqueous NaCl, saturated aquesous $NaHCO_3$ and then saturated aqueous NaCl. The dichloromethane extract was dried over $Na_2SO_4$, filtered, and concentrated on a rotary evaporator to provide 390 mg of the desired material.

EXAMPLE 5

General Procedure for Volatilizing Compounds from Halogen Bulb

A solution of drug in approximately 120 µL dichloromethane is coated on a 3.5 cm×7.5 cm piece of aluminum foil (precleaned with acetone). The dichloromethane is allowed to evaporate. The coated foil is wrapped around a 300 watt halogen tube (Feit Electric Company, Pico Rivera, Calif.), which is inserted into a glass tube sealed at one end with a rubber stopper. Running 60 V of alternating current (driven by line power controlled by a variac) through the bulb for 5-12 s or 90 V for 2.5-3.5 s affords thermal vapor (including aerosol), which is collected on the glass tube walls. (When desired, the system is flushed through with argon prior to volatilization.) Reverse-phase HPLC analysis with detection by absorption of 225 nm light is used to determine the purity of the aerosol.

Table 1, which follows, provides data from drugs volatilized using the above-recited general procedure.

TABLE 1

| COMPOUND | AEROSOL PURITY | AEROSOL MASS |
| --- | --- | --- |
| Indomethacin Methyl Ester | 99% | 1.44 mg |
| Indomethacin Ethyl Ester | >99% | 3.09 mg |
| Indomethacin Norcholine Ester | 100% | 2.94 mg |
| Ketoprofen Methyl Ester | 99% | 4.4 mg |
| Ketoprofen Ethyl Ester | 99.65% | 4.11 mg |
| Ketoprofen Norcholine Ester | 100% | 2.6 mg |
| Ketorolac Methyl Ester | 100% | 3.17 mg |
| Ketorolac Ethyl Ester | >99% | 5.19 mg |
| Ketorolac Norcholine Ester | 100% | 1.64 mg |
| Apomorphine Diacetate-HCl | 94% | 1.65 mg |
| Apomorphine Diacetate | 96.9% | 2.03 mg |

EXAMPLE 6

General Procedure for Hydrolysis Studies of Drug Esters

Drug ester (20 µL, 10 mM acetonitrile) is added to 1 mL PBS solution (pH 7.5) at room temperature. At intermittent time points, an aliquot of the resulting mixture is injected into an HPLC to obtain the ratio of drug ester to drug acid or drug alcohol. An Arrhenius plot of the data provides a $t_{1/2}$ for hydrolysis. Table 2 below provides $t_{1/2}$ values for a variety of compounds.

TABLE 2

| COMPOUND | $t_{1/2}$ |
| --- | --- |
| Ketoprofen Methyl Ester | >48 h |
| Ketoprofen Ethyl Ester | >48 h |
| Ketoprofen Norcholine Ester | 315 min. |
| Ketorolac Methyl Ester | >48 h |
| Ketorolac Ethyl Ester | >48 h |
| Ketorolac Norcholine Ester | 14 min |
| Indomethacin Methyl Ester | >48 h |
| Indomethacin Ethyl Ester | >48 h |
| Indomethacin Norcholine Ester | 315 min. |
| Apomorphine Diacetate | >48 h |

EXAMPLE 7

General Procedure for Human Serum Hydrolysis Studies of Drug Esters

Human serum (2.34 mL) is placed in a test tube. To the serum is added 260 µL of a 10 mM solution of drug ester in acetonitrile. The tube is placed in a 37° C. incubator, and at various time points a 500 µL aliquot is removed. The aliquot is mixed with 500 µL methanol, and the mixture is vortex mixed and centrifuged. A sample of the supernatant is analyzed by HPLC obtain the ratio of drug ester to drug acid or drug alcohol. An Arrhenius plot of the data provides a $t_{1/2}$ for hydrolysis. Table 3 below provides $t_{1/2}$ values for a variety of compounds.

TABLE 3

| COMPOUND | $t_{1/2}$ |
| --- | --- |
| Ketoprofen Methyl Ester | 144 min |
| Ketoprofen Ethyl Ester | 224 min |
| Ketoprofen Norcholine Ester | 37 s |
| Ketorolac Ethyl Ester | 90 min |
| Ketorolac Norcholine Ester | 13 s |
| Indomethacin Methyl Ester | >48 h |
| Indomethacin Ethyl Ester | >48 h |
| Indomethacin Norcholine Ester | 23 min |
| Apomorphine Diacetate | 76.2 s |

EXAMPLE 8

General Procedure for Screening Drug Esters for Aerosolization Preferability Drug ester (1 mg) is dissolved or suspended in a minimal amount of a suitable solvent (e.g., dichloromethane or methanol). The solution or suspension is pipetted onto the middle portion of a 3 cm by 3 cm piece of aluminum foil. The coated foil is wrapped around the end of a 1½ cm diameter vial and secured with parafilm. A hot plate is preheated to approximately 300° C., and the vial is placed on it foil side down. The vial is left on the hotplate for 10 s after volatilization or decomposition has begun. After removal from the hotplate, the vial is allowed to cool to room temperature. The foil is removed, and the vial is extracted with dichloromethane followed by saturated aqueous $NaHCO_3$. The organic and aqueous extracts are shaken together, separated, and the organic extract is dried over $Na_2SO_4$. An aliquot of the organic solution is removed and injected into a reverse-phase HPLC with detection by absorption of 225 nm light. A drug ester is preferred for aerosolization where the purity of the drug ester aerosol isolated by this method is greater than 85%. Such a drug ester has a decomposition index less than 0.15. The decomposition index is arrived at by subtracting the percent purity (i.e., 0.85) from 1.

The invention claimed is:
1. A condensation aerosol for delivery of drug ester,
   wherein the drug ester is an ester of a drug selected from the group consisting of aceclofenac, alclofenac, alminoprofen, amfenac, aspirin, benoxaprofen, bermoprofen, bromfenac, bufexamac, butibufen, bucloxate, carprofen, cinchophen, cinmetacin, clidanac, clopriac, clometacin, diclofenac, diflunisal, etodolac, fenclozate, fenoprofen, flutiazin, flurbiprofen, ibuprofen, ibufenac, indomethacin, indoprofen, ketoprofen, ketorolac, loxoprofen, meclofenamate, naproxen, oxaprozin, pirprofen, prodolic acid, salsalate, sulindac, tofenamate, tolmetincoated, apomorphine, baclofen, levodopa, carbidopa, and thioctate;
   wherein the aerosol is formed by heating a composition containing the drug ester coated on a solid support to produce a vapor and cooling the vapor to form a condensation aerosol comprising particles;
   wherein the particles comprise at least 10 percent by weight of the drug ester and less than 5 percent by weight of drug ester degradation products; and
   wherein the condensation aerosol has an MMAD between 0.2 and 5 microns.

2. The condensation aerosol according to claim 1, wherein the condensation aerosol has an MMAD between 1 and 3 microns.

3. The condensation aerosol according to claim 1, wherein the geometric standard deviation around the MMAD is less than 2.0.

4. The condensation aerosol according to claim 1, wherein the composition further comprises a pharmaceutically acceptable excipient.

5. The condensation aerosol according to claim 1, wherein the drug ester is an ester of a drug selected from the group consisting of indomethacin, ketoprofen, ketorolac, and apomorphine.

6. The condensation aerosol according to claim 5, wherein the condensation aerosol has an MMAD between 1 and 3 microns.

7. The condensation aerosol according to claim 5, wherein the geometric standard deviation around the MMAD is less than 2.0.

8. The condensation aerosol according to claim 5, wherein the composition further comprises a pharmaceutically acceptable excipient.

9. The condensation aerosol according to claim 5, wherein the drug ester is selected from the group consisting of indomethacin methyl ester, indomethacin ethyl ester, and indomethacin norcholine ester.

10. The condensation aerosol according to claim 5, wherein the drug ester is selected from the group consisting of ketoprofen methyl ester, ketoprofen ethyl ester, and ketoprofen norcholine ester.

11. The condensation aerosol according to claim 5, wherein the drug ester is selected from the group consisting of ketorolac methyl ester, ketorolac ethyl ester, and ketorolac norcholine ester.

12. The condensation aerosol according to claim 5, wherein the drug ester is apomorphine diacetate.

13. A method of producing a drug ester aerosol comprising:
  a. coating a composition containing the drug ester on a solid support, wherein the drug ester is an ester of a drug selected from the group consisting of aceclofenac, alclofenac, alminoprofen, amfenac, aspirin, benoxaprofen, bermoprofen, bromfenac, bufexamac, butibufen, bucloxate, carprofen, cinchophen, cinmetacin, clidanac, clopriac, clometacin, diclofenac, diflunisal, etodolac, fenclozate, fenoprofen, flutiazin, flurbiprofen, ibuprofen, ibufenac, indomethacin, indoprofen, ketoprofen, ketorolac, loxoprofen, meclofenamate, naproxen, oxaprozin, pirprofen, prodolic acid, salsalate, sulindac, tofenamate, tolmetincoated, apomorphine, baclofen, levodopa, carbidopa, and thioctate;
  b. heating the coated composition to form a vapor; and
  c. allowing the vapor to cool to produce a condensation aerosol comprising particles, wherein the particles comprise less than 5 percent by weight of drug ester degradation products and wherein the condensation aerosol has an MMAD between 0.2 and 5 microns.

14. The method according to claim 13, wherein the condensation aerosol has an MMAD between 1 and 3 microns.

15. The method according to claim 13, wherein the coated composition comprises at least 10 percent by weight of the drug ester.

16. The method according to claim 13, wherein the composition further comprises a pharmaceutically acceptable excipient.

17. The method according to claim 13, wherein the drug ester is an ester of a drug selected from the group consisting of indomethacin, ketoprofen, ketorolac, and apomorphine.

18. The method according to claim 17, wherein the condensation aerosol has an MMAD between 1 and 3 microns.

19. The method according to claim 17, wherein the coated composition comprises at least 10 percent by weight of the drug ester.

20. The method according to claim 17, wherein the composition further comprises a pharmaceutically acceptable excipient.

21. The method according to claim 17, wherein the drug ester is selected from the group consisting of indomethacin methyl ester, indomethacin ethyl ester, and indomethacin norcholine ester.

22. The method according to claim 17, wherein the drug ester is selected from the group consisting of ketoprofen methyl ester, ketoprofen ethyl ester, and ketoprofen norcholine ester.

23. The method according to claim 17, wherein the drug ester is selected from the group consisting of ketorolac methyl ester, ketorolac ethyl ester, and ketorolac norcholine ester.

24. The method according to claim 17, wherein the drug ester is apomorphine diacetate.

* * * * *